United States Patent [19]
Oftring et al.

[11] Patent Number: 5,898,084
[45] Date of Patent: Apr. 27, 1999

[54] PREPARATION OF N-ACYLAMINOCARBOXYLIC ACIDS AND N-ACYLAMINOSULFONIC ACIDS AND ALKALI METAL SALTS THEREOF

[75] Inventors: Alfred Oftring, Bad Dürkheim; Martin aus dem Kahmen, Ludwigshafen, both of Germany

[73] Assignee: BASF Aktiengesellschaft, Ludwigshafen, Germany

[21] Appl. No.: 08/981,476

[22] PCT Filed: Jul. 2, 1996

[86] PCT No.: PCT/EP96/02888

§ 371 Date: Jan. 13, 1998

§ 102(e) Date: Jan. 13, 1998

[87] PCT Pub. No.: WO97/03043

PCT Pub. Date: Jan. 30, 1997

[30]  Foreign Application Priority Data

Jul. 13, 1995 [DE] Germany ................................ 19525512

[51] Int. Cl.$^6$ ........................... C07C 51/16; C07C 51/097
[52] U.S. Cl. ........................... 562/104; 562/524; 562/525
[58] Field of Search ..................................... 562/104, 524, 562/525

[56] References Cited

U.S. PATENT DOCUMENTS 4,380,646   4/1983   Franzmann .

*Primary Examiner*—Johann Richter
*Assistant Examiner*—Taofiq A. Solola
*Attorney, Agent, or Firm*—Oblon, Spivak, McClelland, Maier & Neustadt, P.C.

[57] ABSTRACT

The process for preparing an N-acylaminocarboxylic or N-acylaminosulfonic acid or an alkali metal salt thereof from an alkali metal aminocarboxylate or aminosulfonate and a carboxylic glyceride comprises (a) preparing a suspension of the solid anhydrous alkali metal aminocarboxylate or aminosulfonate in the carboxylic glyceride, (b) adding a strong base to the suspension to form an alkali metal N-acylaminocarboxylate or N-acylaminosulfonate, and (c) if desired, preparing the free N-acylaminocarboxylic or N-acylaminosulfonic acid therefrom in a conventional manner by adding an acid.

10 Claims, No Drawings

PREPARATION OF N-ACYLAMINOCARBOXYLIC ACIDS AND N-ACYLAMINOSULFONIC ACIDS AND ALKALI METAL SALTS THEREOF

This application is a 371 of PLT/EP96/02888 filed Jul. 2, 1996.

The present invention relates to an improved process for preparing N-acylaminocarboxylic acids and N-acylaminosulfonic acids and their alkali metal salts from the alkali metal salts of, respectively, aminocarboxylic acids and aminosulfonic acids and certain carboxylic esters.

WO-A 95/07881 discloses that alkali metal salts of N-acylsarcosine can be prepared by acylating an alkali metal sarcosinate with alkyl carboxylates, in particular methyl carboxylates, in the presence of basic catalysts such as sodium methoxide or potassium ethoxide at from 80 to 200° C. The disadvantage of this method is the use of alkyl carboxylates, for example methyl oleate, which has to be expensively prepared in an upstream synthesis step and may have to be purified.

It is an object of the present invention to provide an efficient and economical process for preparing N-acylaminocarboxylic acids and N-acylaminosulfonic acids and alkali metal salts thereof in sufficient purity in good space-time yields starting from readily obtainable and inexpensive starting materials.

We have found that this object is achieved by a process for preparing an N-acylaminocarboxylic or N-acylaminosulfonic acid or an alkali metal salt thereof from an alkali metal aminocarboxylate or aminosulfonate and a carboxylic ester by (a) preparing a suspension of the solid anhydrous alkali metal aminocarboxylate or aminosulfonate in the carboxylic ester, (b) adding a strong base to this suspension to form an alkali metal N-acylaminocarboxylate or N-acylaminosulfonate, and (c) if desired, preparing the free N-acylaminocarboxylic or N-acylaminosulfonic acid therefrom in a conventional manner by adding an acid, which comprises using a carboxylic ester that is a carboxylic glyceride.

Step (a) is carried out, for example, by introducing the carboxylic glyceride and the solid anhydrous alkali metal aminocarboxylate or aminosulfonate into a suitable vessel made of glass or some other material and processing the contents with a customary suspending stirrer into a finely divided suspension.

The suspension of step (a) can also be prepared by mixing the carboxylic glyceride and an aqueous solution of the alkali metal aminocarboxylate or aminosulfonate in a suitable vessel made of glass or some other material and then, by heating and applying a vacuum, removing the water from the mixture as rapidly as possible. Surprisingly, there is very little saponification of the carboxylic glyceride to the alkali metal salt of the underlying carboxylic acid. The advantage of using such an aqueous solution is that industrially produced aqueous solutions of alkali metal aminocarboxylates or aminosulfonates can be used without further preparation such as spray drying. Nor are there any problems associated with the handling of solids, such as dusting or uniform metering.

Typically, the suspension of step (a) is prepared from equivalent or substantially equivalent amounts of the alkali metal aminocarboxylate or aminosulfonate, based on the acyl groups in the carboxylic glyceride, and of the carboxylic glyceride; that is, typically in a molar ratio of 3:1 (in the case of pure triglycerides). An excess of carboxylic glyceride, for example as diluent, is normally not necessary. In some cases, it can be advantageous to have an excess of alkali metal aminocarboxylate or aminosulfonate, for example up to a molar ratio of 5:1.

In step (b), the suspension prepared in step (a) is admixed with a strong base in a catalytic, equimolar or greater amount to initiate the reaction. The base is usually added after or during the heating-up of the suspension to the reaction temperature, but may also be added even in the course of the preparation of the suspension in step (a), for example together with the alkali metal aminocarboxylate or aminosulfonate, or shortly before the suspension is heated up. The base can be used as a solid substance or in dissolved form, for example in an organic solvent such as an alcohol.

The amount of strong base used is preferably from 0.5 to 150 mol %, in particular from 1 to 50 mol % or from 50 to 130 mol %, preferably from 5 to 20 mol % or from 70 to 110 mol %, based on the alkali metal aminocarboxylate or aminosulfonate. Depending on the specific conditions of the reaction, it can be better to use the strong base in a catalytic or equimolar amount. The strong base used can be a single species or a mixture of different bases.

Suitable strong bases include in particular:

alkoxides, especially alkali metal alkoxides of $C_1$-$C_4$-alkanols, eg. sodium methoxide, sodium ethoxide, sodium isopropoxide or potassium tert-butoxide;

hydrides, eg. sodium hydride, sodium borohydride or lithium aluminum hydride;

alkali metal or alkaline earth metal hydroxides, eg. sodium hydroxide, potassium hydroxide, lithium hydroxide or calcium hydroxide;

alkali metal carbonates, eg. sodium carbonate, potassium carbonate or lithium carbonate;

amide salts, eg. lithium diisopropylamide;

organolithium compounds such as alkyllithium compounds, eg. n-butyllithium or methyllithium, or phenyllithium.

Of these, alkoxides are preferred.

The reaction in step (b) is carried out in a relatively mild temperature range, usually at from 50 to 200° C., in particular at from 80 to 180° C., especially at from 120 to 160° C. The reaction is normally carried out under atmospheric pressure; although autogenous or elevated pressure is possible, it has no distinct advantages.

Within 1 to 2 hours from the addition of the base there is usually no longer any carboxylic glyceride detectable in the reaction mixture by analytical methods, for example infrared (IR) spectroscopy. The glycerol produced in the course of the reaction from the carboxylic glyceride either remains in the reaction mixture or is partly or wholly removed by working up in a conventional manner, depending on whether its presence in the resulting product does or does not interfere with the intended use.

After the reaction has ended, the reaction mixture typically has the form of a viscous paste. This paste can be dissolved by adding water after the temperature has decreased, for example to 80–100° C. The result is, for example, an approximately 30–40% strength by weight aqueous solution of an alkali metal N-acylaminocarboxylate or N-acylaminosulfonate.

If the free N-acylaminocarboxylic or N-acylaminosulfonic acid is to be obtained, it is prepared in step (c) from the alkali metal salt in a conventional manner by adding an acid. Suitable acids include in particular mineral acids such as sulfuric acid, phosphoric acid or hydrochloric acid, which are usually added at room temperature to the aqueous solution of the alkali metal N-acylaminocarboxylate or N-acylaminosulfonate, so as to obtain a pH within the range from about 0 to 3, in particular from 1 to 2. This typically results in a milky creamy emulsion. This emulsion is advantageously separated at a slightly elevated temperature, for example at from 40 to 70° C., using a customary phase separation aid, for example a ketone such as isobutyl methyl ketone or methyl ethyl ketone, an alkanol such as n-butanol, isobutanol or sec-butanol, an ether such as methyl tert-butyl ether or diisopropyl ether, a $C_1$-$C_4$-alkyl acetate or propionate or an acetoacetic ester, which may be added together with the acid or after the emulsion has formed. Phase separation aids of this type are low-boiling compounds which have little if any miscibility with water and are inexpensive to use on an industrial scale.

The process of the present invention performs particularly well when the alkali metal aminocarboxylate used is the lithium or especially the sodium or potassium salt of an aliphatic aminocarboxylic acid having from 2 to 10 carbon atoms, preferably from 3 to 6 carbon atoms, in particular of valine, leucine, norleucine, glycine, alanine, β-alanine, ε-aminocaproic acid, α-aminoisobutyric acid, sarcosine (N-methylglycine), aspartic acid, glutamic acid or iminodiacetic acid. But it is also possible to use the sodium or potassium salts of other natural α-amino acids, of oligopeptides or of aromatic or cycloaliphatic aminocarboxylic acids, for example anthranilic acid, phenylglycine, phenylalanine or 1-aminocyclohexane-1-carboxylic acid. Aminocarboxylic acids for the purposes of the present invention are particularly compounds having a primary or secondary amino group and one or two carboxyl groups per molecule; however, it is also possible in principle to use compounds having more than one amino group and/or more than two carboxyl groups, in which case the amount of carboxylic glyceride depends on the number of amino groups. The carboxyl groups are virtually all in salt form.

The process of the present invention performs likewise particularly well when the alkali metal aminosulfonate used is the lithium or especially the sodium or potassium salt of an aliphatic aminosulfonic acid having from 2 to 10 carbon atoms, preferably from 2 to 4 carbon atoms. Of particular interest here are the corresponding salts of taurine (2-aminoethanesulfonic acid) and N-methyltaurine. Like the aminocarboxylic acid used, the aminosulfonic acid used, which is likewise virtually completely in the alkali metal salt form, may have a plurality of amino and/or sulfonic acid groups.

Suitable carboxylic glycerides include in particular customary, naturally occurring fatty acid glycerides. These are usually mono-, di- or in particular triglycerides of saturated or unsaturated monocarboxylic acids having from 6 to 30, in particular from 10 to 22, carbon atoms, or mixtures thereof. Examples of the underlying monocarboxylic acids are lauric acid, myristic acid, palmitic acid, stearic acid, oleic acid, linoleic acid and linolenic acid. In mono-, di- and triglycerides the glycerol is esterified with, respectively, one, two or three of these carboxylic acids. In di- and triglyceride molecules, identical or different carboxylic acids may be esterified with the glycerol.

In nature, these carboxylic glycerides, in particular triglycerides, occur as vegetable or animal fats or oils, usually with a high proportion of unsaturated carboxylic acids, in particular oleic acid. Especially suitable are soybean oil, colza oil, olive oil, sunflower oil, cottonseed oil, groundnut oil, linseed oil, rapeseed oil, copra oil, palm fruit oil, castor oil, bovine tallow and fish oil. But it is also possible to use triglycerides with a high proportion of saturated shorter-chain fatty acids (eg. $C_{12}$, $C_{14}$) such as coconut oil or palm kernel oil with success in the process of the present invention.

The process of the present invention can be used to prepare sufficiently pure N-acylaminocarboxylic acids and N-acylaminosulfonic acids and also alkali metal salts thereof or mixtures of such compounds with different acyl esters and/or different basic aminocarboxylic and aminosulfonic acids in a simple and economical manner. Compounds of this type are known to be useful as emulsifiers or surfactants in a wide range of technical fields.

The process of the present invention affords good space-time yields of the desired products without prior conversion of the carboxylic glyceride into a low-alkyl carboxylate, for example the corresponding methyl ester. The relatively mild temperature regime means no decomposition reactions leading to the loss of yield and darkening of product color. The reactions go to completion in a significantly shorter time.

The use of carboxylic glycerides as inexpensive and easily handled acylating components and the avoidance of salt in the acylation make the process of the present invention extremely attractive for use on an industrial scale.

EXAMPLE NO. 1

232.5 g (0.25 mol) of colza oil and 13.5 g (0.075 mol) of sodium methoxide (as 30% strength by weight solution in methanol) were initially charged and heated to 180° C. 125 g (1.125 mol) of sodium sarcosinate (prepared from a spray-dried sodium sarcosinate solution in water) were then added a little at a time with vigorous stirring. On completion of the addition the reaction mixture was thoroughly stirred, a water jet vacuum was applied, and stirring was continued until glyceride could no longer be detected in the reaction mixture (after about 2–4 hours). The reaction mixture was then cooled down to 80–100° C., admixed with 700 ml of water and acidified (pH 1.5) with concentrated sulfuric acid. 240 ml of methyl ethyl ketone were added to form two phases. The organic phase was separated off and the solvent was removed in a rotary evaporator, leaving 227 g of a yellowish oil containing N-oleoylsarcosinic acid as main constituent.

EXAMPLE NO. 2

465 g (0.5 mol) of colza oil and 167 g (1.5 mol) of sodium sarcosinate were added together and thoroughly stirred with an Ultra Turrax. Following addition of 18 g (0.1 mol) of sodium methoxide (as 30% strength by weight solution in methanol) the contents were carefully heated to 140° C. A water jet vacuum was applied at the same time. After the reaction had ended (about 2–5 hours), the reaction mixture was cooled down to 80–100° C., admixed with 700 ml of water and acidified (pH 1.5) with concentrated sulfuric acid. 240 ml of methyl ethyl ketone were added to form two phases. The organic phase was separated off and the solvent was removed in a rotary evaporator, leaving 510 g of a yellowish oil containing N-oleoylsarcosinic acid as main constituent.

EXAMPLE NO. 3

232.5 g (0.25 mol) of colza oil and 13.5 g (0.075 mol) of sodium methoxide (as 30% strength by weight solution in methanol) were initially charged and heated to 180° C. 125 g (1.125 mol) of sodium sarcosinate (prepared from a spray-dried sodium sarcosinate solution in water) were then added a little at a time with vigorous stirring. On completion of the addition the reaction mixture was thoroughly stirred, a water jet vacuum was applied, and stirring was continued until glyceride could no longer be detected in the reaction mixture (about 2–4 hours). The reaction mixture was then cooled down to 80–100° C., admixed with 1000 ml of water and stirred until a clear aqueous solution had formed. The final weight was 1350 g of solution containing sodium N-oleoylsarcosinate as main constituent.

We claim:

1. A process for preparing an N-acylaminocarboxylic or N-acylaminosulfonic acid or an alkali metal salt thereof from an alkali metal aminocarboxylate or aminosulfonate and a carboxylic ester by
   (a) preparing a suspension of the solid anhydrous alkali metal aminocarboxylate or aminosulfonate in the carboxylic ester,
   (b) adding a strong base to this suspension to form an alkali metal N-acylaminocarboxylate or N-acylaminosulfonate, and
   (c) if desired, preparing the free N-acylaminocarboxylic or N-acylaminosulfonic acid therefrom in a conventional manner by adding an acid,
which comprises using a carboxylic ester that is a carboxylic glyceride.

2. A process as claimed in claim 1 wherein, in step (a), a suspension is prepared from equivalent or substantially equivalent amounts of the alkali metal aminocarboxylate or aminosulfonate, based on the acyl groups in the carboxylic glyceride, and of the carboxylic glyceride.

3. A process as claimed in claim 1 wherein, in step (b), the strong base is used in an amount of from 0.5 to 150 mol %, based on the alkali metal aminocarboxylate or aminosulfonate.

4. A process as claimed in claim 1 wherein, in step (b), the strong base is used in an amount of from 5 to 20 mol % or from 70 to 110 mol %, based on the alkali metal aminocarboxylate or aminosulfonate.

5. A process as claimed in claim 1 wherein, in step (b), the strong base used is an alkali metal alkoxide.

6. A process as claimed in claim 1 wherein the reaction of step (b) is carried out at from 50 to 200 ° C.

7. A process as claimed in claim 1 wherein the alkali metal aminocarboxylate used is the sodium or potassium salt of an aliphatic aminocarboxylic acid having from 2 to 10 carbon atoms.

8. A process as claimed in claim 1 wherein the alkali metal aminosulfonate used is the sodium or potassium salt of an aliphatic aminosulfonic acid having from 2 to 10 carbon atoms.

9. A process as claimed in claim 1 wherein the carboxylic glyceride used is a mono-, di- or triglyceride of a saturated or unsaturated monocarboxylic acid having from 6 to 30 carbon atoms.

10. A process as claimed in claim 1, wherein in suspension (a) the molar ratio of the alkali metal aminocarboxylate or aminosulfonate to the acyl groups in the carboxylic glyceride is from 3:1 to 5:1.

* * * * *